(12) United States Patent
Hornack et al.

(10) Patent No.: US 8,298,588 B2
(45) Date of Patent: Oct. 30, 2012

(54) DIETARY SUPPLEMENT CONTAINING ALKALINE ELECTROLYTE BUFFERS

(76) Inventors: Janmarie Hornack, Overland Park, KS (US); Lawrence E. Dorman, Grain Valley, MO (US)

( * ) Notice: Subject to any disclaimer, the term of this patent is extended or adjusted under 35 U.S.C. 154(b) by 256 days.

(21) Appl. No.: 12/082,510

(22) Filed: Apr. 11, 2008

(65) Prior Publication Data

US 2008/0193565 A1     Aug. 14, 2008

Related U.S. Application Data

(60) Division of application No. 10/679,535, filed on Oct. 3, 2003, which is a continuation of application No. 09/706,005, filed on Nov. 3, 2000, now abandoned.

(60) Provisional application No. 60/164,085, filed on Nov. 6, 1999.

(51) Int. Cl.
*A01N 59/26* (2006.01)

(52) U.S. Cl. ........ 424/602; 424/601; 424/610; 424/663; 424/675; 424/682; 424/686; 424/687; 424/688; 424/709; 424/714

(58) Field of Classification Search .................. None
See application file for complete search history.

(56) References Cited

U.S. PATENT DOCUMENTS

| | | | |
|---|---|---|---|
| 4,568,547 A | 2/1986 | Herschler | |
| 4,579,843 A | 4/1986 | Ehrenpreis et al. | |
| 5,306,511 A | 4/1994 | Whang | |
| 5,424,074 A * | 6/1995 | Koli et al. | 424/464 |
| 5,455,050 A * | 10/1995 | Beyerle et al. | 424/682 |
| 5,849,346 A | 12/1998 | Hornack | |
| 5,853,748 A | 12/1998 | New | |
| 5,888,514 A | 3/1999 | Weisman | |
| 5,914,130 A | 6/1999 | Whang | |
| 6,123,944 A | 9/2000 | Chen et al. | |
| 6,139,872 A | 10/2000 | Walsh | |
| 6,162,787 A | 12/2000 | Sorgente et al. | |
| 6,224,871 B1 | 5/2001 | Hastings et al. | |
| 6,261,600 B1 | 7/2001 | Kirschner et al. | |
| 6,346,519 B1 | 2/2002 | Petrus | |
| 2003/0180389 A1 | 9/2003 | Phillips | |

FOREIGN PATENT DOCUMENTS

WO     WO 99/21437     *  5/1999

OTHER PUBLICATIONS

Shangraw R. F., Public Health Reports Supplement, 1987, p. 46-50.*

* cited by examiner

*Primary Examiner* — Kade Ariani
(74) *Attorney, Agent, or Firm* — John C. McMahon

(57) ABSTRACT

An improved dietary and/or therapeutic supplement composition comprising a quantity of a dietary and/or therapeutic supplement agent having a pH that upon ingestion with food or a beverage would limit the effectiveness of the agent and a sufficient amount of an alkaline electrolyte additive is provided in combination with the agent to raise the pH of the composition to a level of from about 8 to about 12.5 to increase the effectiveness and functional utilization of the agent while the composition is in the person's stomach. The supplement composition is designed to provide for optimum utilization of a dietary and/or therapeutic supplement agent when taken orally with food or a beverage.

4 Claims, No Drawings

DIETARY SUPPLEMENT CONTAINING ALKALINE ELECTROLYTE BUFFERS

CROSS-REFERENCE TO RELATED APPLICATIONS

This application is a division of Ser. No. 10/679,535, filed Oct. 3, 2003, which is incorporated into the present application by reference thereto.

BACKGROUND OF THE INVENTION

1. Field of the Invention

The present invention relates to improve dietary or therapeutic supplements for improving a person's health and well-being, and to a method for neutralizing deleterious acid conditions that occur when a person ingests foods and beverages in conjunction with therapeutic dietary supplements. As a result, an excessive acid condition in the person's stomach that could interfere with the beneficial effect of the dietary supplement is avoided. Dietary and therapeutic supplements such as herbs, and certain compounds known to promote health and well-being are utilized more efficiently in an alkaline environment.

2. Description of the Prior Art

It has been widely accepted that dietary therapeutic supplements are recommended for a variety of the healing properties and for boosting the body's natural abilities to react to disease and protect the body's natural function. It has also been widely accepted that the body requires certain pH balances in various systems within the body, such as blood stream, stomach, various organs, skin, etc. The ability of the body to properly digest and utilize various nutrients from food, beverages or from dietary supplements, is directly related to the pH of the body and its various systems.

Many dietary and therapeutic supplements contain directions that they should be taken with a meal. In fact, most doctors, such as those caring for women who might be pregnant, when prescribing such supplements, indicate to the patients that the supplement should be taken with meals. Even when supplements and medicines are taken on an empty stomach with a beverage, the ability to digest and adsorb are dependent upon pH stability.

Literature references such as Reverse Aging (Sang Whang), Alkalize or Die (Dr. Theodore Baroody) and Acid and Alkaline (Herman Aihara), indicate that most of the food and beverages ingested at meals leads to an acid pH in the body. The body then attempts to counteract these conditions by releasing alkaline buffers stored in the body to neutralize pH in the body's various systems to a "normal" range for that system, i.e. blood, stomach, urine, colon, pancreas, adrenals etc. Additionally, the body utilizes any alkaline pH nutrient that is ingested with the meal to balance the pH. However, the naturally occurring buffers in the body are normally inadequate to assure that the utilization environment of the supplement in an individual's body is sufficiently alkaline to protect the supplement agent.

There is a large consumer market for products that include, for example, calcium carbonate and/or magnesium oxide to aid in counteracting the acid pH that results from digestion of foods and beverages thus causing acid toxic waste in a person's body. Additionally, devices have been provided for consumer use such as machines that produce alkaline water to aid in these acid conditions, and products created to aid with this problem (such as Acid pHree™).

In the Whang (U.S. Pat. Nos. 5,306,511 and 5,914,130), the patentee states that the elimination of acid wastes from the body is greatly enhanced through the use of alkaline water and alkaline minerals in the form of sodium and potassium bicarbonate. Additionally, claims are made to prevent increased acidity in various systems of the body through the use of blood buffers and to aid the body's pH value from experiencing extreme fluctuations. The acid toxic waste is believed to be the primary or major contributing factor in certain adult degenerative states in the body such as diabetes and kidney disease.

Whang further asserts in the '511 and '130 patents that by maintaining a blood buffer, and resisting changes in hydrogen ion concentrations, a positive effect is realized by balance and stabilization of pH in the body. Whang also indicates that it is not only the amount of minerals taken that is a factor, but also the mating that is significant.

In the Homack U.S. Pat. No. 5,849,346, patentee discloses an additive for beverages which includes potassium hydroxide and a mixture of electrolyte ions such as the alkaline minerals (sodium, potassium, calcium and magnesium) in various forms (hydroxides, chlorides, carbonates, gluconates, bicarbonates, phosphates, sulfates, chelates, di-phosphates, oxides and stearates). Homack's additive is said to be useful for increasing the normally acidic pH of the beverage to a value of 9.5 to as much as 14.0 in beverages.

SUMMARY OF THE INVENTION

The present invention relates to a unique dietary and/or therapeutic supplement composition for promoting a person's health and well-being, and to a method of enhancing the utilization of such supplements by incorporation of a sufficient quantity of alkaline buffering agents in the supplement to increase the ability of the body to more readily accept and utilize all of the supplement healing agents at a more absorbable level. This invention may be utilized in tablet, capsule, powder or liquid forms. A preferred supplement formulation is in tablet form, although essentially equivalent results may be obtained with a liquid supplement.

The improved dietary and/or therapeutic supplement composition of the present invention comprises a combination of a supplement that promotes health and well-being in conjunction with alkaline minerals and/or electrolytes which function as buffers upon ingestion of the supplement, particularly when the supplement is taken at mealtime. The improved supplement composition stabilizes the pH ranges in the person's body to acceptable levels, and minimizes pH fluctuations in the user's stomach, particularly when the supplements are taken at mealtime, so that supplements or medicaments may be utilized appropriately at optimum levels. The additives for the supplement composition may be combined with supplements of choice which address the preventative or healing task required. The improved supplement composition hereof further may include appropriate amounts of vitamins in various forms, as for example, Vitamin C, which effectively aid the body in the utilization of certain dietary supplements. There is mounting evidence that supplements which are ingested in combination with Vitamin C provides better patient results.

The present invention comprises an improved dietary and/or therapeutic supplement composition in combination, a quantity of a dietary and/or therapeutic supplement agent having a pH that upon ingestion would limit the effectiveness of the agent, and a sufficient amount of an electrolyte additive in combination with the agent to raise the pH of the combination to a level of at least about 8 to increase the effectiveness of the agent upon ingestion of the composition.

It is an important object of the present invention to provide an improved supplement composition and method of enhancing the functionality of dietary supplements for optimum utilization of the supplement agent(s) by the various systems of the body.

Another object of the invention is to provide an improved supplement composition which assists in developing a more alkaline environment inside the body for enhancement of the excretion of acid toxic waste.

Another object of the invention is to provide a better environment for supplement agents during the digestion process and for the movement of dietary supplements throughout the body. The alkaline electrolytes added to the supplement are preferably one or more of the four electrolytes normally present in the body and that enable fluid to move extracellular, intercellular and intracellular.

Another object of the invention is to combine a number of desirable dietary and/or therapeutic supplement agents with alkaline buffers that are present in respective proper ratios as required by the body to permit most effective utilization of the supplement, so that a person can buy the combined supplement composition and need not buy several separate bottles of supplements to achieve the same goal.

Another object of the invention is to provide a supplement composition that creates a better pH range overall in the body, so that the body is not losing buffering agents at an undesirable rapid pace, thus aiding the body in decreasing the degree and rate of the aging and disease processes.

DETAILED DESCRIPTION OF THE INVENTION

The present invention provides an improved supplement composition and method for improving the utilization by a person of supplements which promote healing and well-being of a person upon ingestion of the supplement composition. Moreover, the invention supplies electrolyte buffers that are essential for health (one to four alkaline minerals, all of which are electrolytes required for functioning of the body).

The supplement composition of the present invention is operable to enhance stabilization of pH in the person's body, to decrease fluctuations of pH in a person's system, to reduce acid toxic waste, and to improve the balance and level of alkaline minerals and increase the buffering capabilities of electrolytes.

There is evidence that for a therapeutic supplement such as methylsulfonylmethane ("MSM") to properly and efficiently function as expected, an acid pH in the person's digestive system has an adverse effect on the functionality of the MSM. Also, it has been established that the body requires alkaline minerals to perform functions in addition to the raising of pH and the buffering of acid toxic waste. For example, it is known that calcium is required for rebuilding bone mass and that a lack of usable calcium may result in disease such as osteoporosis. A less known, but nevertheless important fact, is that magnesium is required by the body to properly utilize the calcium and to aid in the prevention of heart attacks. The initiative in this area of study has been done by Paul Mason of Patterson, Calif. The National Academy of Sciences (NAS) is conducting a study for the FDA on the dietary benefits of calcium and magnesium. Mr. Mason has asserted that there is a global pattern of disease from a deficiency in magnesium. Research at the California Department of Health Services has suggested that the addition of 10 ml to 30 mg/liter of magnesium to water per day may account for a significant drop that is being experienced demographically in the rate of heart disease. It is also well known that alkaline minerals are required by the body in amounts that are not normally ingested from an individual's normal diet. Sodium is the exception, as many Americans ingest more sodium in their daily food than required, due to increasingly high intake of processed foods and restaurant food.

When a therapeutic supplement is needed for preventive and healing properties, and the supplement is taken with a meal (as often indicated by the directions for that supplement, by the healing practitioner, or by habit), the body must first be able to:

A. Digest the food and beverage
B. Buffer the acid waste
C. Carry and potentiate the supplement throughout the body
D. Retain potency of the supplement to be utilized for its intended purpose, rather then by being used by the body as a buffering agent first.

The constituency, amount and relative ratios of supplements to provide a desired therapeutic effect, and the form in which the supplements are taken may vary, often depending upon the minimum level of RDA for at least certain of the supplements, as well as the nature of the condition being alleviated by the substance. Thus, in providing an optimal pH balance in the person's body, upon ingestion of supplements and the like, the pH of the supplement or medicament itself and the balance required by the body (Guyton, Textbook of Medical Physiology and Homack) must be taken into account.

In producing tablets, capsules, powders or liquids containing a therapeutic supplement that is useful for preventive or health improvement, the pH of the supplement or medicament itself must be considered first. Next, the pH value that is ideal for ingestion of the supplement or medicament at the mealtime must be taken into account. To that end, appropriate alkaline electrolytes by weight are added to the supplement agent as are required to provide an ideal pH in the person's stomach upon ingestion of the supplement with the meal. The pH should always be 8.0 or higher when the supplement composition is ingested along with a meal. The ideal range in the stomach is 8.0 to 10.5, but may go as high as 12.5, depending upon the nature of the supplement or medicine.

No change is made to the supplements themselves; the supplement agent(s) are combined with the requisite alkaline electrolytes in proper ratios to manage factors A, B and D above. In order to improve the ability of the body to move the supplement through the blood stream, many companies practicing the art, have combined their supplements with Vitamin C in various forms, which is known to act as an oxidizing agent and to aid in moving the various nutrients throughout the bloodstream by increasing the oxygen. Studies indicate that use of Vitamin C in combination with supplements aid in increased promotion of healing. Research was published in this area by Linus Pauling, winner of the Nobel Prize for chemistry and recipient of other major scientific honors. The companies that have not included Vitamin C in their formulas, many times suggest or indicate that taking Vitamin C in conjunction with their supplement is recommended, and research on the subject supports this theory. Research also indicates that the use of bioflavonoids potentiate and protect the Vitamin C adsorption. The way that bioflavonoids increase the effectiveness of Vitamin C is believed to be the way in which they act to restore oxidized Vitamin C by working with glutathione.

Regarding the other 3 items (A, B and D), very little attention has previously been given to these matters.

Although sodium can be incorporated in the formulation as one of the electrolytes, it is not preferred because most individuals already exceed their need for sodium in the diet on a daily basis, which can contribute to hypertension. The present invention, while allowing for use of all of the electrolytes to boost pH in conjunction with other supplements, preferably contains calcium, magnesium and potassium, as these tend to be lacking in the diets of many people.

By combining one of the alkaline electrolytes (potassium, calcium, magnesium, and sodium) in the mix of the dietary and/or therapeutic supplement, the body utilizes the electrolyte component(s) to balance acidity and eliminate toxic waste, thereby allowing the nutrient or supplement to be fully utilized for its intended objective. Movement of the dietary supplement is also improved by the provision of the electrolytes: intracellular, intercellular and extracellular. This further contributes to the increased utilization of the dietary supplement.

There are many therapeutic supplements that benefit from the present invention. Two exemplary supplement agents are glucosamine and MSM (methylsulfonylmethane).

Glucosamine is naturally occurring as a mucopolysaccharide in the body and is required to produce chondroitin. Found in the body in synovial fluid (which lubricates joints), glucosamines are subunits of glucosamino glycans (GAG's). These are synthesized from glutamine and carbohydrate. The amino acid must be replaced in the diet or by a dietary supplement, to stimulate the body's production of hyaluronic acids (HA's). These products have analgesic effects and promote the anabolic behavior in chrondrocytes. With diseases of age, the HA concentration tends to become depleted and replacement with glucosamine is believed to aid in long term repair. It has been suggested that glucosamine functions to build ligaments, increase fluid in the joints, and improve heart valves, tendons, eyes, nails, skin, digestive tract membranes and bone.

Chondroitin sulfates are commonly combined with glucosamines because of a perceived synergistic effect obtained with the combination. The pH range for this type of combined supplement is typically around 3.34 to about 3.39. Upon ingestion of the glucosamine/chondroitin formulation, the body immediately seeks to adjust the pH balance, resulting in depletion in electrolytes from the user's system, causing more toxic waste, and elimination of a portion of the therapeutic supplement.

Combining glucosamine/chondroitin with designed amounts of less expensive, high pH electrolyte minerals in accordance with the present invention, aids in balancing the pH in the body without depletion of intracellular and extracellular electrolytes from the body and serves to enhance elimination of acid toxic waste. The alkaline material buffers these acids, so that the glucosamine may benefit the problem of the body with the rapid movement of the supplement into all cell structures of the body (intracellular, extracellular and intercellular). The same is true for chondroitin sulfates, which are, in the practice of the art, commonly tableted with the glucosamine. The pH range for this type of combined supplement is typically around 3.34-3.39. If the alkaline electrolytes are not incorporated with the supplement and are taken separately from the supplement, the body will immediately release the intra and extracellular buffers, causing more acid toxin waste, and the elimination of a portion of the supplement with the waste.

Additionally, glucosamine and chondroitin supplements are administered for their ability to decrease pain in joints, which for example results from arthritic conditions (U.S. Pat. No. 5,840,715, Florio). When a combination of glucosamine and chondroitin is taken along with food or beverage as directed, the resulting increase in body acid due to pH value of foods and beverages, has an adverse effect on the effectiveness of the active ingredient supplement. This increase in body acid has another deleterious effect in that it also tends to cause additional deposits of toxins in the very areas of the body which are susceptible to arthritic conditions. The glucosamine and chondroitin, which were administered to relieve the arthritic symptoms, are not as effective and the toxins being generated which tend to deposit in the body's weakest areas are adding to the problem. (Whang and Aihara) Therefore, an added benefit is obtained by combining alkaline minerals with an active ingredient such as glucosamine and chondroitin because of the buffering action of the alkaline minerals which results in a part of the acidic deposit eventually beginning to clear as the body corrects its pH.

Furthermore, by combining the relatively high pH alkaline electrolytes with the dietary and/or therapeutic supplement, the body pH is immediately stabilized and the supplement is moved through the system with the electrolytes for balancing and the movement of body fluids. Utilization of the supplement is at a much higher rate than would otherwise be the case if the formulation of the invention had been used.

Another primary example of the benefits of this invention is in connection with the therapeutic supplement MSM (methylsulfonylmethane). MSM is an organic sulfur, generally found in a pH range of 7.2 to 7.4. In the body, sulfur is the fourth most prevalent mineral. The sulfur in the body appears to be reduced during the aging process. At maturity, the levels of MSM found in the hormonal fluid may be as low as 0.5 ppm. In U.S. Pat. Nos. 4,514,421, 4,559,329, 4,568,547, 4,973,605, and 5,071,878, Herschler has claimed that a level of at least 1.0 ppm be maintained for health and effective immune system. The skin, bones and muscles of the body contain about ½ of the sulfur found in the total body. Sulfur is needed for producing collagen. Herschler states that there is evidence of the benefits of MSM for various health related conditions for animals and man. These include but are not limited to: human tissue pliancy; tumor control; formation of disulfide bonds for connective tissue integrity; repair and restoration of damaged tissue; aid in reducing reaction to allergens; aid in relieving constipation; improving condition of arthritic patients; relieving cramping and sores; reducing hypertension; and many other benefits. Other literature sources indicate that sulfur is required for the creation of new cells, repair of tissue, cartilage, and organs and is found as a component in the blood.

Herschler and other sources indicate that studies were performed with MSM alone compared with MSM plus Vitamin C. Patients taking the combination responded more quickly to treatment. Herschler also presented information indicating that the sulfur present in the food stuffs are highly volatile and processing or cooking effect the availability for the body in order to replace the sulfur, MSM is a preferred embodiment for use in the body.

Dr. S. W. Jacob, in Am. Acad. Meri. Pred., 1983, the current status of MSM medicine has recommended to control hyperacidity and heartburn. Jacob's recommendation is 3000 mg per day. Because MSM is relatively expensive, it is not a practical antacid.

When MSM, taken as a dietary supplement, is combined with the alkaline electrolytes in proper ratios for use by the body, the pH of the tablet, powder, capsule or liquid is increased substantially. A preferred MSM tablet formulation in accordance with the present invention is:

In each of two tablets:
1000 mg MSM (standard recommended dose—although ranges are given for body weight)
780 mg Ascorbic Acid (Vitamin C) & 20 mg Bioflavonoid (Vitamin P, to Potentiate Vitamin C)

100 mg Calcium Carbonate
50 mg Potassium Gluconate
50 mg Magnesium Oxide
with appropriate binders and coatings, well known to those skilled in the art of tableting.

In the example above, the pH of the tablet is significantly increased. In addition, a recommended dose of Vitamin C for this particular supplement is provided. Normally the pH of the ascorbic acid is about 3.23 and the pH of the MSM about 7.2. Thus, a necessary element which aids in rapid promotion of healing is included in the formulation and at the same time the pH of the tablet is increased to about 8.63 by incorporation of required electrolyte constituents in proper ratios. This is a preferred pH range for the combined supplement and electrolyte composition to be taken prior to mealtime to counteract the acid wastes of the digestion process and falls within the range for a better utilization of supplements. In certain instances, it may be desirable to increase the pH to an even higher value by adding a greater amount of respective alkaline minerals as described above, or by utilizing other forms of these minerals, such as hydroxides, sulfates, carbonates, bicarbonates, gluconates, oxides, stearates, chelates, di-phosphates, chlorides and phosphates.

In the MSM example above, the pH has been substantially increased to prevent extreme fluctuation of the pH in the body at mealtime, thus enabling the MSM to be more efficiently utilized by the body to perform the task/tasks for which the supplement targeted. With the present invention, hyperacidity/heartburn as discussed by Dr. Jacob has been managed, and permitting the more expensive MSM supplement to target other problems. Since the pH of MSM is typically lower than the pH of the four alkaline mineral additives in any form, a smaller quantity of the alkaline minerals are required to accomplish the same goal of controlling hyperacidity at a much lower cost because of the differential in price of MSM and alkaline mineral additives.

In a study of patients taking pure MSM for therapeutic relief of arthritic conditions it was found that by administering the MSM in the formulation described above, the amount of the MSM required to obtain relief was cut in half over those patients taking pure MSM.

In another formulation, glucosamine and MSM are combined for their respective healing properties and pain relief. Additional supplements known for pain and joint relief are included, such as Boswellia extract, dl-phenylalaine, ginseng extract, ginkgo biloba extract and borage powder.

MSM—Glucosamine Capsule Formula
500 mg glucosamine sulfate
900 mg MSM
20 mg 20% Boswellia extract
100 mg dl-phenylalanine
60 mg ascorbic acid
5 mg citrus bioflavonoids
50 mg magnesium carbonate
50 mg potassium carbonate
100 mg calcium gluconate
10 mg 5:1 ginseng extract
10 mg 24% ginkgo biloba
15 mg pyroxdine hydrochloride
180 mg 10% gla borage powder In the above formulation, the constituent ingredients that minimize and relieve pain are combined with the ascorbic acid, biflavonoids and pyroxdine hydrochloride (synergistic constituents) and are measured for combined pH, the value obtained is 3.75. When the alkaline constituents are added to the active ingredients, the pH value is increased to 8.0. This allows the body to counteract the negative effects of acid toxins thus decreasing body acid toxins and allowing the active constituents to be more fully utilized and falls within the optimal therapeutic range.

Other kinds of dietary or therapeutic supplements can be utilized at greater levels by the body if the body's pH balance is stabilized in the appropriate pH ranges, and this can occur even at mealtime when the supplements are ingested by utilizing in accordance with the improved supplement composition of the present invention. In many respects, the actual pH of the supplement or medicine is not the controlling issue, other than that the electrolyte additives shift the pH range substantially upwards to facilitate the movement of the supplement and aid the body in the ability to more fully utilize the supplement. Some of these supplements include, but are not limited to:

Vitamins such as B3, B complex, B12, C, niacin and the like.

Minerals and trace minerals zinc, copper, boron and similar elements.

Enzymes such as pepsin, CoEnzyme Q10 and others.

Amino Acids such as L-Taurine, L-Lysine and more.

Whole food products containing phytonutrients used as dietary supplement, such as the "Complete Fruit and Vegetable Formula" of HealingMD, Inc., Sherman Oaks, Calif.

Herbs and herbal extracts.

Beneficial bacterial and yeast products for replication in the intestinal tract such as lactobacillus acidophilus.

Mixed dietary and therapeutic supplements and other nutrient products such as mixtures of the above listed constituent ingredients.

Certain medicaments may also be improved through the use of these electrolytes, particularly when the movement of the therapeutic agent throughout the body quickly is a desirable attribute.

Examples of the pH of dietary or therapeutic supplements prior to combination with required amounts of useful alkaline minerals are set forth in the table below. When an individual takes any one of these supplements with the meal, the body begins the digestion process of the supplement and the meal and the body begins to try to eliminate the acid toxic waste and buffer the system. The body will utilize any buffer that can be found within the food, supplement, and after that will begin to draw the alkaline minerals from within the system itself. Therefor, by providing the alkaline buffer in combination with the dietary or therapeutic supplement, substantially all of the supplement is retained intact, to aid in healing, for preventive medicine, to assist in the digestion and elimination process and to slow down the problems associated with acid pH, as described by Hornack, Whang, Baroody and Aihara.

Table of pH of exemplary of dietary and/or therapeutic supplements

1 B Complex 7.2 Ascorbic Acid 3.23 Soy Lecithin 6.8 Emu Oil 6.5 Zinc 3.5 St. John's Wart 4.9 Slippery Elm Bark 4.1 Glucosamine 5.5 Gingko Bilboa Leaf Extract 5.1 Niacin 3.4 Vitamin E 6.1 Multivitamins 5.0-6.0

The pH ranges of the alkaline minerals that are preferably included as a part of a dietary or therapeutic supplement composition in the method of the present invention are from 7.2 to 14.0. These include potassium (9.69 and up depending upon the form of potassium); magnesium (7.20 and up depending upon the form of magnesium); and calcium (8.28 and up depending upon the form of calcium). Although sodium is not included in the preferred formulation because most people in the United States already have too much sodium in their diets, sodium as an electrolyte may be included in the supplement composition in those instances where certain individuals need more sodium. For example, for those in need of supplemental sodium beyond what is available in their normal diet, or for athletes who may require more sodium, then a sodium electrolyte can be incorporated in the dietary and/or therapeutic supplement composition as an additional component to raise the pH of the composition. An example of sodium used by athletes for adding immediate electrolytes, moving fluids, and aiding in reducing lactic acid is Gatorade™.

The pH range preferred (8.0-12.5) can be obtained by using the above minerals in any of the forms available that are approved for pharmaceutical, food grade or potable use. Depending upon the combination of supplements in a tablet, capsule, liquid or powder formula, the amount of the alkaline minerals and the form of the alkaline minerals may be adjusted as required.

Preferred embodiments of combinations of electrolytes in accordance with the present invention, include but are not limited to the following ratios, on a weight to weight basis:

Ca/Mg/K
2/1/1
2/1/1.5
2/1/2
1/0.5/1
1/0.75/1
2/0.75/2
2/1.25/2
1/0.5/0.5
2/0.75/0.75
2/1.25/0.75

The amount of magnesium should equal at least 30% to 100% of the calcium. Since there are many calcium supplements on the market today that do not include magnesium, the present invention in that instance boosts the ratio of the mg/ca, thus aiding in the proper digestion of Ca ingested in other supplements or in the calcium fortified food products.

The amount of potassium electrolyte levels can vary, depending on the supplement that is combined with the potassium additive. Providing a substantial dose of potassium in the formulation assists in counteracting the effects of too much sodium in a person's body, by providing a proper balance of the two elements.

The mineral electrolyte additive or the dietary and/or therapeutic supplement transport as electrolytes throughout the body, giving the increased advantage of easily moving the digested supplements or medicaments along extracellular, intracellular and intercellular paths.

A preferred liquid composition making up 30 ml aliquot is prepared by admixing:
   420 ml of 45% KOH
   10.25 ml $P_2O_5$ (Glass H-a long chain linear polyphosphate) into 200 mL D/I $H_2O$
   1.2 ml NaCl into 125 ml D/I $H_2O$
   1.2 mg CaCl into 100 ml D/I $H_2O$
   3.0 $MgSO_4$ into 150 ml D/I $H_2O$
   3.5 mg NaHCO3 into 100 ml D/I $H_2O$
   0.05 mg bioflavonoid
   3.0 mg methylsulfonylmethane
   bring solution up to 3750 ml total with D/I $H_2O$ In certain instances, it may also be desirable to include 0.01 mg of ascorbic acid in the above formulation.

It is clear that the present invention is well adapted to carry out the object and to obtain the ends and advantages mentioned as well as those inherent therein. While a presently preferred embodiment of the invention has been described for the purposes of this disclosure, it will be recognized that numerous changes may be made which will readily suggest themselves to those skilled in the art and which are encompassed within the spirit of the invention disclosed.

What is claimed and desired to be secured by Letters Patent is as follows:

1. A method of improving uptake of a dietary supplement through the stomach, when the supplement is ingested with at least one of a food and a beverage, the method consisting essentially of:
   a) providing an ingestable mixture, the mixture including:
      i) a quantity of at least one dietary supplement selected from the group consisting of a water soluble acidic vitamin, a bioflavanoid, a mineral, a trace mineral, a whole plant food product containing phytonutrients, and a herb, wherein the dietary supplement has a pH of 6 or less and is in a liquid form; and
      ii) a quantity of a liquid alkaline electrolyte selected from the group consisting of calcium, magnesium and potassium electrolytes; wherein
   b) when the mixture is ingested, the quantity of alkaline electrolyte is sufficient to provide a pH of from about 8.63 to about 12.5 as the mixture is being ingested.

2. The method of claim 1 wherein the quantity of alkaline electrolyte is sufficient to provide a pH of from about 8.63 to about 10.5.

3. The method of claim 1 wherein the alkaline electrolyte is at least one of calcium hydroxide, magnesium hydroxide, potassium hydroxide, calcium chloride, magnesium chloride, potassium chloride, calcium chelate, magnesium chelate, potassium chelate, calcium di-phosphate, magnesium di-phosphate, potassium di-phosphate, calcium oxide, magnesium oxide, potassium oxide, calcium stearate, magnesium stearate, potassium stearate, calcium carbonate, magnesium carbonate, potassium carbonate, calcium gluconate, magnesium gluconate, potassium gluconate, calcium bicarbonate, magnesium bicarbonate, potassium bicarbonate, calcium phosphate, magnesium phosphate, potassium phosphate, calcium sulfate, magnesium sulfate, and potassium sulfate.

4. The method of claim 1 wherein the dietary supplement includes magnesium electrolyte and calcium electrolyte and an amount of the magnesium electrolyte is equal to at least 30% of the calcium electrolyte.

* * * * *